United States Patent
Akasaka et al.

(10) Patent No.: US 11,285,418 B2
(45) Date of Patent: Mar. 29, 2022

(54) AIR PURIFYING APPARATUS AND AIR PURIFYING METHOD

(71) Applicant: Panasonic Intellectual Property Management Co., Ltd., Osaka (JP)

(72) Inventors: Osamu Akasaka, Hyogo (JP); Koki Narihata, Kyoto (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 17/118,649

(22) Filed: Dec. 11, 2020

(65) Prior Publication Data

US 2021/0093990 A1    Apr. 1, 2021

Related U.S. Application Data

(63) Continuation of application No. PCT/JP2019/043912, filed on Nov. 8, 2019.

(30) Foreign Application Priority Data

Dec. 14, 2018  (JP) .............................. JP2018-234784

(51) Int. Cl.
   *B01D 45/12*    (2006.01)
   *B01D 47/06*    (2006.01)
   (Continued)

(52) U.S. Cl.
   CPC .............. *B01D 45/14* (2013.01); *B01D 45/12* (2013.01); *B01D 47/06* (2013.01); *B01D 50/004* (2013.01);
   (Continued)

(58) Field of Classification Search
   CPC .. B01F 3/04007; B01F 3/04014; B01D 45/12; B01D 47/00; B01D 47/06; B01D 50/004
   See application file for complete search history.

(56) References Cited

U.S. PATENT DOCUMENTS 3,292,347 A * 12/1966 Hodgkinson ........... D06F 58/22
                                                     261/83

FOREIGN PATENT DOCUMENTS

| JP | 4-094712 | 3/1992 |
|----|----------|--------|
| JP | 7-229325 | 8/1995 |

(Continued)

OTHER PUBLICATIONS

International Search Report of PCT application No. PCT/JP2019/043912 dated Feb. 4, 2020.

(Continued)

*Primary Examiner* — Robert A Hopkins
(74) *Attorney, Agent, or Firm* — Wenderoth, Lind & Ponack, L.L.P.

(57) ABSTRACT

An air purifying apparatus includes a humidity controller and an intake cooling separator including one or more shafts and an outer wall. The intake cooling separator generates airflow to obtain the humidity-controlled air. The intake cooling separator swirls the obtained air around a first shaft included in the one or more shafts, thereby generating a pressure difference between air included in the obtained air and around the first shaft and air included in the obtained air and around the outer wall, and the pressure difference cools at least a part of the obtained air, and the pressure difference cools at least a part of the obtained air. The intake cooling separator performs centrifugal separation of water droplets generated from the cooled air. The one or more shafts are rotated to generate the airflow, to cause the swirl, and to perform the centrifugal separation.

7 Claims, 8 Drawing Sheets

(51) Int. Cl.
   *B01D 45/14*   (2006.01)
   *B01D 50/00*   (2006.01)
   *B01F 3/04*    (2006.01)
   *B01D 51/06*   (2006.01)
   *B01D 53/26*   (2006.01)
   *F24F 3/16*    (2021.01)
   *F24F 6/00*    (2006.01)
   *F24F 7/00*    (2021.01)
   *F24F 13/22*   (2006.01)

(52) U.S. Cl.
   CPC ........... *B01D 51/06* (2013.01); *B01D 53/265* (2013.01); *B01F 3/04007* (2013.01); *B01F 3/04014* (2013.01); *F24F 3/16* (2013.01); *F24F 6/00* (2013.01); *F24F 7/00* (2013.01); *F24F 13/22* (2013.01); *B01D 2257/80* (2013.01)

(56) References Cited

FOREIGN PATENT DOCUMENTS

| | | |
|---|---|---|
| JP | 11-023020 | 1/1999 |
| JP | 2000-042350 | 2/2000 |
| JP | 2004-066090 | 3/2004 |
| KR | 10-2010-096801 | 9/2010 |
| WO | 2005/075799 | 8/2005 |

OTHER PUBLICATIONS

Extended European Search Report dated Jan. 4, 2022 for the related European Patent Application No. 19896202.9.

* cited by examiner

AIR PURIFYING APPARATUS AND AIR PURIFYING METHOD

BACKGROUND

1. Technical Field

The present disclosure relates to an apparatus that purifies air.

2. Description of the Related Art

To date, air purifying apparatuses that remove from air a gas to be removed are known (see, for example, Japanese Unexamined Patent Application Publication No. 2004-66090 and Japanese Unexamined Patent Application Publication No. 2000-42350).

SUMMARY

It is desirable to provide an air purifying apparatus having a configuration simpler than those of existing air purifying apparatuses.

One non-limiting and exemplary embodiment provides an air purifying apparatus that can realize a configuration simpler than existing configurations.

In one general aspect, the techniques disclosed here feature an air purifying apparatus including: a humidity controller that controls a humidity of air; and an intake cooling separator that includes one or more shafts and an outer wall that surrounds at least a part of the one or more shafts. The intake cooling separator generates airflow to obtain the humidity-controlled air, and thereby the intake cooling separator obtains the humidity-controlled air. The intake cooling separator swirls the obtained air around a first shaft included in the one or more shafts, and thereby the intake cooling separator generates a pressure difference between air included in the obtained air and around the first shaft and air included in the obtained air and around the outer wall. The pressure difference cools at least a part of the obtained air. The intake cooling separator performs centrifugal separation of water droplets that are generated from the cooled air. The one or more shafts are rotated to generate the airflow, to cause the swirl, and to perform the centrifugal separation.

With an air purifying apparatus according to an aspect of the present disclosure, it is possible to realize a configuration simpler than existing configurations.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
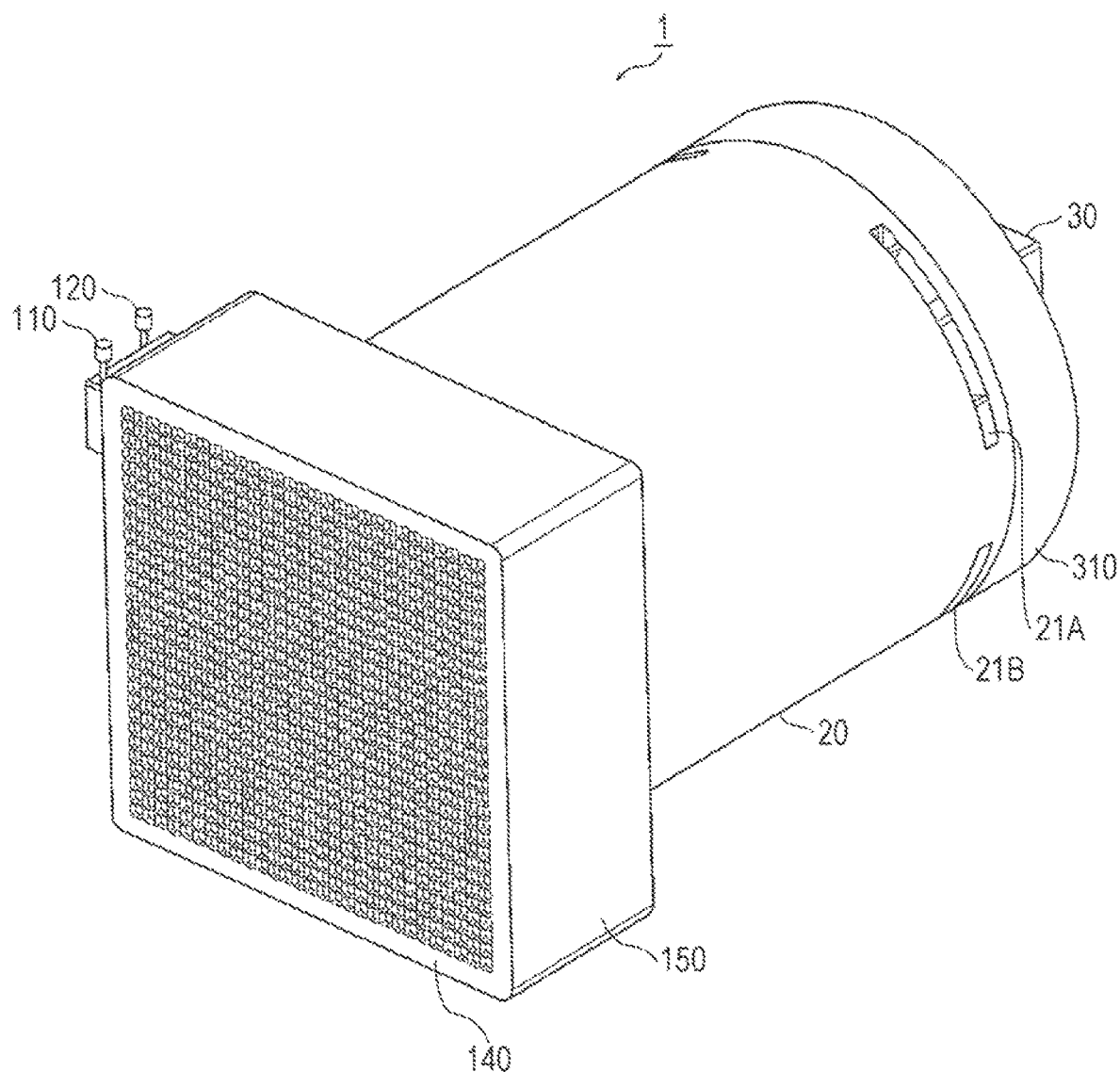
FIG. 1 is an external perspective view of an air purifying apparatus according to a first embodiment.

An air purifying apparatus according to an aspect of the present disclosure includes: a humidity controller that controls a humidity of air; and an intake cooling separator that includes one or more shafts and an outer wall that surrounds at least a part of the one or more shafts. The intake cooling separator generates airflow to obtain the humidity-controlled air, and thereby the intake cooling separator obtains the humidity-controlled air. The intake cooling separator swirls the obtained air around a first shaft included in the one or more shafts, and thereby the intake cooling separator generates a pressure difference between air included in the obtained air and around the first shaft and air included in the obtained air and around the outer wall. The pressure difference cools at least a part of the obtained air. The intake cooling separator performs centrifugal separation of water droplets that are generated from the cooled air. The one or more shafts are rotated to generate the airflow, to cause the swirl, and to perform the centrifugal separation.

With the air purifying apparatus described above, when a gas to be removed is a water-soluble gas, the gas to be removed included in air dissolves in the water droplets that are generated by cooling. Then, the water droplets including the gas to be removed are separated from the air. Thus, the air purifying apparatus described above can remove from air the gas to be removed. Moreover, the air purifying apparatus described above need not have a scrubber device, an activated carbon filter, a thermal storage layer, and the like, which are necessary for exiting air purifying apparatuses.

Accordingly, with the air purifying apparatus described above, it is possible to realize an air purifying apparatus having a configuration simpler than existing configurations.

The humidity controller may include a gas sensor that detects a predetermined gas, a temperature and humidity sensor that detects a temperature and a humidity of the air, and a humidifier that humidifies the air based on a result of detection by the gas sensor and a result of detection by the temperature and humidity sensor.

Thus, the air purifying apparatus can purify polluted air in accordance with the absence/presence of a gas to be removed and the temperature and humidity of air.

The outer wall may have a discharge hole for discharging, to the outside, the water droplets.

Thus, the air purifying apparatus can discharge the water droplets, which include a gas to be removed, to the outside.

The one or more shafts may be the first shaft, the intake cooling separator may include a propeller fan and a blade fan, the propeller fan may be attached to the first shaft and may rotate when the first shaft rotates, the blade fan may be attached to the first shaft and may rotate when the first shaft rotates, rotation of the propeller fan may generate the airflow, and rotation of the blade fan may cause the swirl.

Thus, the air purifying apparatus can purify polluted air more effectively.

The one or more shafts may include the first shaft, a second shaft, and a third shaft; the intake cooling separator may include an intake section that includes the second shaft and generates the airflow, a cooler that includes the first shaft and causes the swirl, and a separator that includes the third shaft and performs the centrifugal separation; and the second shaft may be rotated to generate the airflow, the first shaft may be rotated to cause the swirl, and the third shaft may be rotated to perform the centrifugal separation.

Thus, with the air purifying apparatus, it is possible to provide an air purifying apparatus having improved maintainability.

The intake section may include a propeller fan, the cooler may include a blade fan, the propeller fan may be attached to the second shaft and may rotate when the second shaft rotates, the blade fan may be attached to the first shaft and may rotate when the first shaft rotates, the rotation of the propeller fan may generate the airflow, and the rotation of the blade fan may cause the swirl.

Thus, the air purifying apparatus can purify polluted air more efficiently.

An air purifying method according to an aspect of the present disclosure includes: controlling a humidity of air; generating airflow to obtain humidity-controlled air, thereby obtaining the humidity-controlled air; swirling the obtained air around a first shaft included in the one or more shafts, thereby generating a pressure difference between air included in the obtained air and around the first shaft and air included in the obtained air and around an outer wall that surrounds at least a part of the one or more shafts, the pressure difference cooling at least a part of the obtained air; and performing centrifugal separation of water droplets that are generated from the cooled air, wherein the one or more shafts are rotated to generate the airflow, to cause the swirl, and to perform the centrifugal separation.

With the air purifying method described above, when a gas to be removed is a water-soluble gas, the gas to be removed included in air dissolves in the water droplets that are generated by cooling. Then, the water droplets including the gas to be removed are separated from air. Thus, it is possible to remove from air the gas to be removed by using the air purifying method described above. Moreover, an air purifying apparatus that purifies polluted air by using the air purifying method described above need not have a scrubber device, an activated carbon filter, a thermal storage layer, and the like, which are necessary for exiting air purifying apparatuses.

Accordingly, with the air purifying method described above, it is possible to realize an air purifying apparatus having a configuration simpler than existing configurations.

Hereafter, specific examples of an air purifying apparatus according to an aspect of the present disclosure will be described with reference to the drawings. Embodiments described herein each represent a specific example of the present disclosure. Accordingly, numbers, shapes, components, arrangement and connection of components, steps, and the order of steps are each an example and do not limit the present disclosure. Components that are included in the embodiments described below and that are not described in the independent claims are optional components. Each figure is a schematic view and is not necessarily drawn strictly.

First Embodiment

Figure 2:
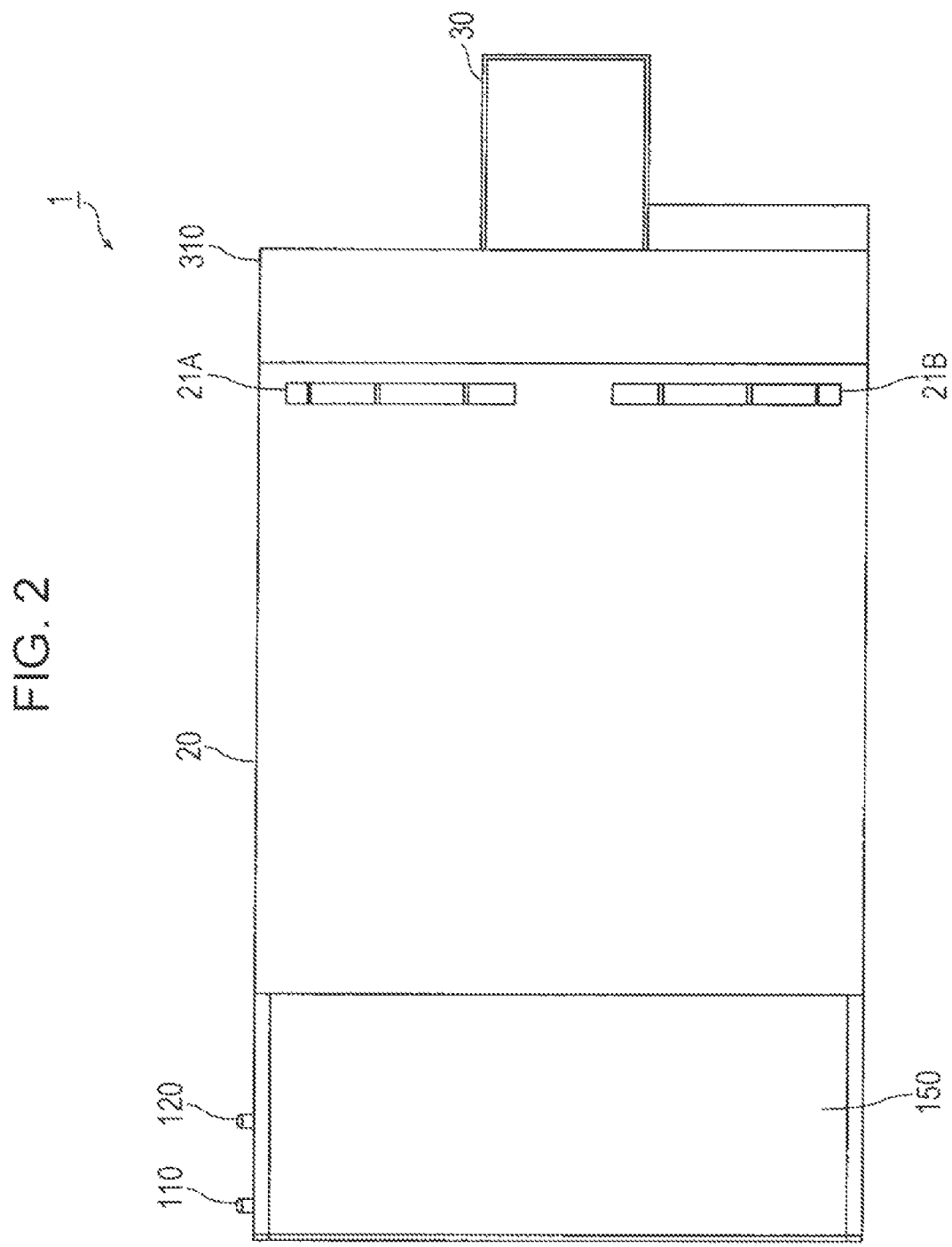
FIG. 2 is an external side view of the air purifying apparatus according to the first embodiment.

FIG. 1 is an external perspective view of an air purifying apparatus 1 according to a first embodiment. FIG. 2 is an external side view of the air purifying apparatus according to the first embodiment.

As illustrated in FIGS. 1 and 2, the air purifying apparatus 1 includes an outer wall 20 shaped like a side surface of a cylinder, a duct 150 to which a metal mesh 140 is attached and whose cross section is a quadrangle, a protective wall 310 shaped like a side surface of a cylinder whose radius and axis are the same as those of the outer wall 20, a motor housing 30 that houses a motor, a gas sensor 110, and a temperature and humidity sensor 120. The metal mesh 140 is attached to one of opening surfaces of the duct 150.

The gas sensor 110 is disposed on a side surface of the duct 150 and detects a predetermined gas that is included in air around the air purifying apparatus 1 and that is to be removed when purifying air. The predetermined gas is a water-soluble gas that is, for example, a water-soluble sulfur oxide (SOx) and/or a water-soluble nitrogen oxide (NOx).

The temperature and humidity sensor 120 is disposed on a side surface of the duct 150 and detects the temperature and humidity of air around the air purifying apparatus 1.

The outer wall 20 has discharge holes 21 extending through the outer wall 20. In FIGS. 1 and 2, the discharge holes 21 are a discharge hole 21A and a discharge hole 21B.

Figure 3:
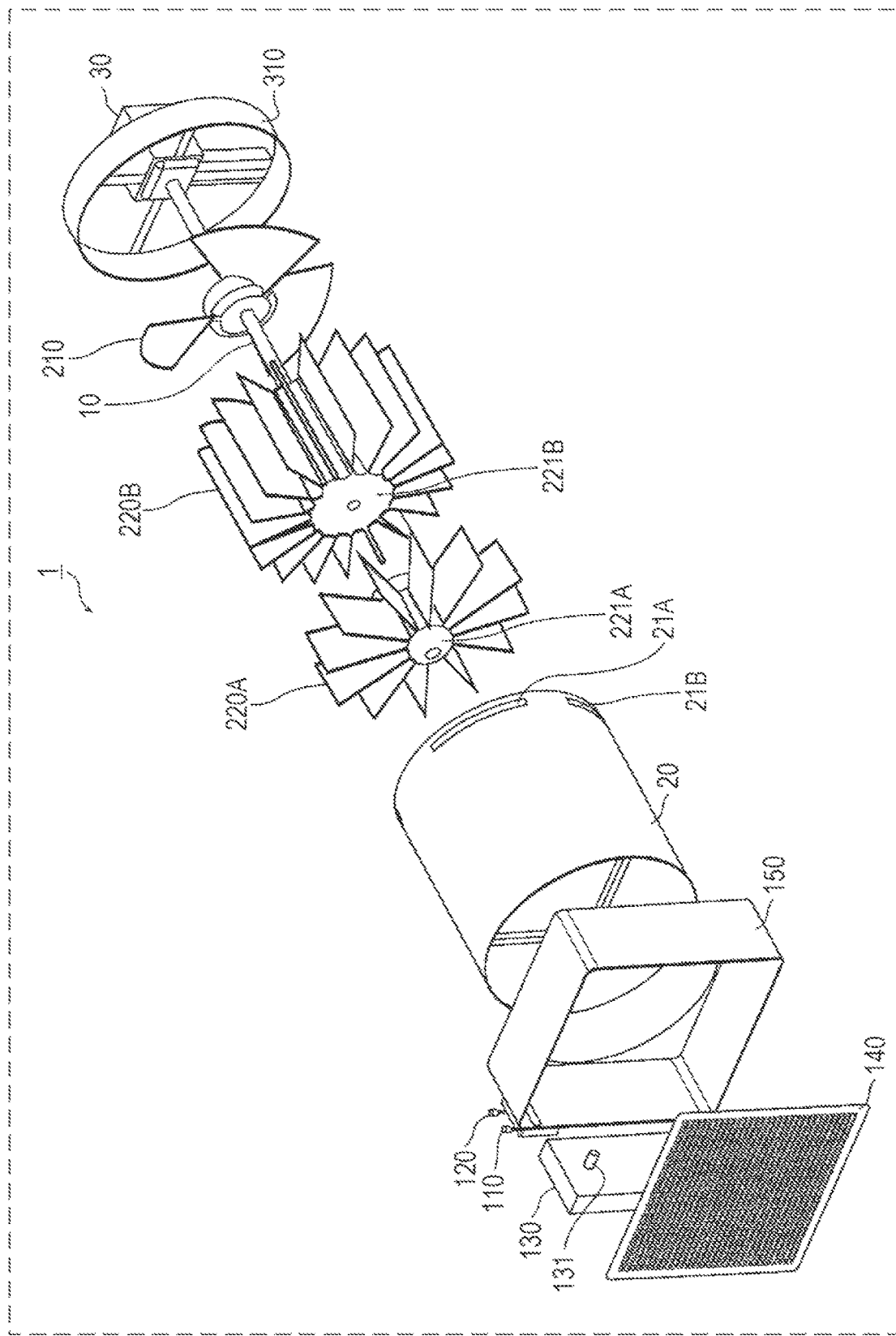
FIG. 3 is an exploded perspective view of the air purifying apparatus according to the first embodiment.

FIG. 3 is an exploded perspective view of the air purifying apparatus 1.

As illustrated in FIG. 3, the air purifying apparatus further includes, inside thereof, a shaft 10, a propeller fan 210, a first blade fan 220A, a second blade fan 220B, and a humidifier 130.

Figure 4:
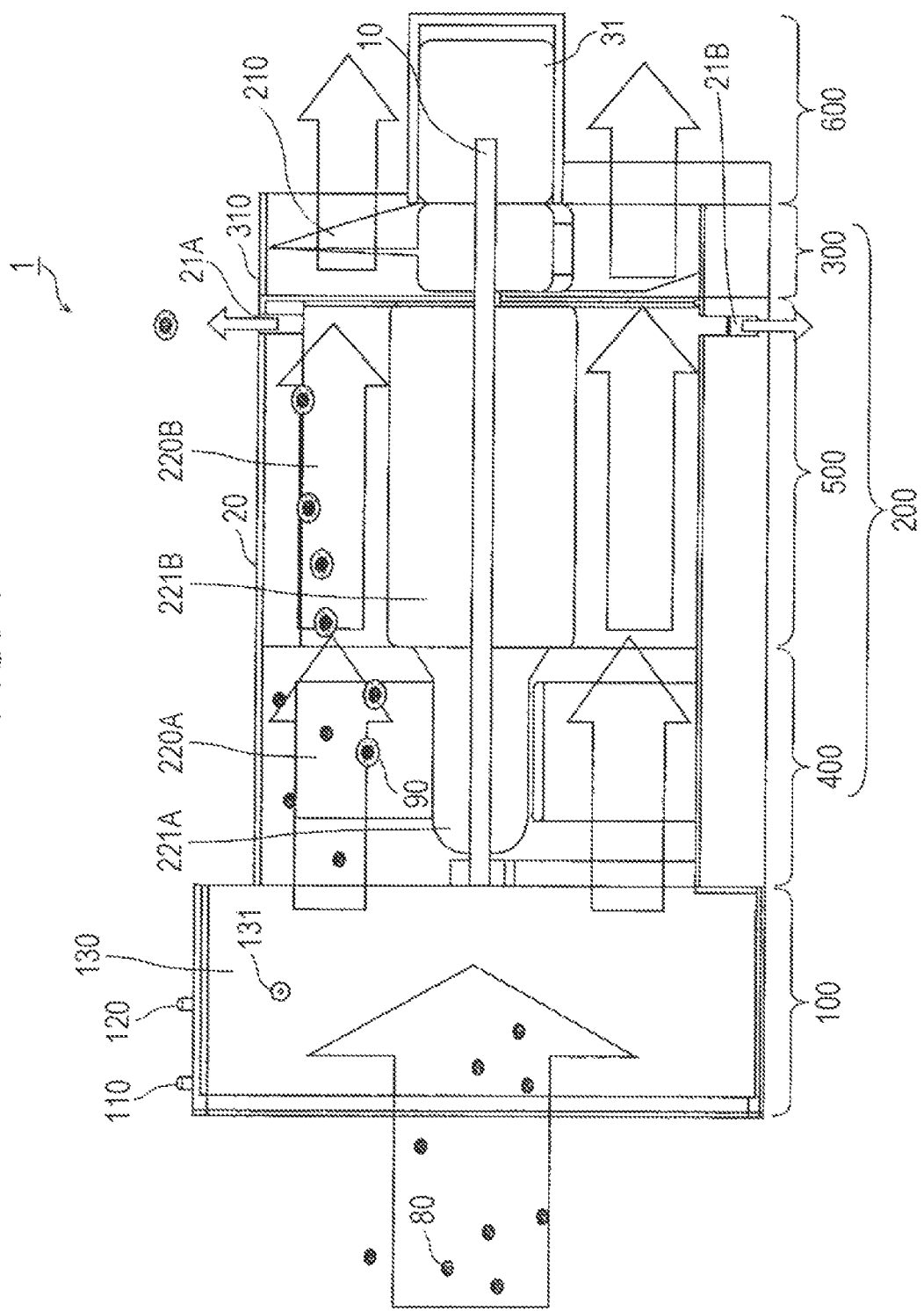
FIG. 4 is a sectional view of the air purifying apparatus according to the first embodiment.

The shaft 10 is a bar-shaped rigid body that is fixed to the rotation shaft of a motor so as to rotate together with the rotation shaft of the motor. The motor is housed in the motor housing 30. The motor is not illustrated in FIG. 3. The motor corresponds to a motor 31 illustrated in FIG. 4. The shaft 10 rotates around the axis thereof. The shaft 10 is fixed to the rotation shaft of the motor so that the axis thereof coincides with the axis of the outer wall 20. As illustrated in FIG. 4, at least a part of the shaft 10 is surrounded by the outer wall 20.

The propeller fan 210 is fixed to the shaft 10 so as to rotate together with the shaft 10. The propeller fan 210 and the shaft 10 integrally rotate with the axis of the shaft 10 as the rotation axis. The propeller fan 210 has one or more blades that rotate and thereby generate airflow having a component in the rotation-axis direction of the propeller fan 210. The propeller fan 210 is fixed to the shaft 10 at a position surrounded by the protective wall 310.

The first blade fan 220A is fixed to the shaft 10 so as to rotate together with the shaft 10. The first blade fan 220A and the shaft 10 integrally rotate with the axis of the shaft 10 as the rotation axis. The first blade fan 220A has one or more blades that rotate and thereby generates airflow that swirls around the rotation axis. The first blade fan 220A is fixed to the shaft 10 at a position surrounded by the outer wall 20.

The second blade fan 220B is fixed to the shaft 10 so as to rotate together with the shaft 10. The second blade fan 220B and the shaft 10 integrally rotate with the axis of the shaft 10 as the rotation axis. The second blade fan 220B has one or more blades that rotate and thereby generate airflow that swirls around the rotation axis. The second blade fan 220B is fixed to the shaft 10 at a position surrounded by the outer wall 20.

The radius of a shaft body 221A of the first blade fan 220A in a cross section perpendicular to the rotation axis is smaller than the radius of a shaft body 221B of the second blade fan 220B in a cross section perpendicular to the rotation axis.

To the shaft 10, the first blade fan 220A, the second blade fan 220B, and the propeller fan 210 are fixed, sequentially from the duct 150 side toward the motor housing 30 side.

The humidifier 130 humidifies air in the duct 150 by spraying mist from a nozzle 131 and is disposed in the duct 150. The humidifier 130 humidifies air based on the result of detection by the gas sensor 110 and the result of detection by the temperature and humidity sensor 120. The humidifier 130 may be, for example, an ultrasonic mist atomizer.

FIG. 4 is a sectional view of the air purifying apparatus 1. FIG. 4 illustrates, in addition to the sectional view of the air purifying apparatus 1, a schematic view that overlaps the sectional view and that shows arrows indicating flow of air in the air purifying apparatus 1, dust particles 80 included in air, and water droplets 90 that have condensed with the dust particles 80 as nuclei.

As illustrated in FIG. 4, the air purifying apparatus 1 includes a humidity controller 100, an intake cooling separator 200, and a shaft rotator 600. The intake cooling separator 200 includes an intake section 300, a cooler 400, and a separator 500.

The shaft rotator 600 includes the motor housing 30, the motor 31 housed in the motor housing 30, and a part of the shaft 10 (a margin for fixing the shaft 10 to the rotation shaft of the motor 31). The shaft rotator 600 rotates the shaft 10 by instructing the motor 31 to rotate the rotation shaft of the motor 31.

The shaft rotator 600 may instruct the motor 31 to rotate the rotation shaft thereof when the gas sensor 110 described below detects a predetermined gas. That is, the shaft rotator 600 may receive from the gas sensor 110 a signal of detection by the gas sensor 110 and may instruct the motor 31 to rotate the rotation shaft thereof when the signal indicates a predetermined value.

The intake section 300 includes the protective wall 310, the propeller fan 210, and a part of the shaft 10. As the shaft 10 rotates, the propeller fan 210 rotates together with the shaft 10, and the intake section 300 generates airflow such that air flows in the direction indicated by the arrows in FIG. 4.

The humidity controller 100 includes the duct 150, the metal mesh 140, the gas sensor 110, the temperature and humidity sensor 120, and the humidifier 130. Outside air flows through the metal mesh 140 into the humidity controller 100 due to the airflow generated by the intake section 300. Airborne dust particles are included in the air that flows into the humidity controller 100. Typical air includes 2000 dust particles, each having a diameter in the range of 0.5 μm to 0.8 μm, per cubic centimeter.

The humidity controller 100 controls the humidity of air in the humidity controller 100. That is, by using the humidifier 130, the humidity controller 100 humidifies air in the humidity controller 100 based on the result of detection by the gas sensor 110 and the result of detection by the temperature and humidity sensor 120. To be more specific, only when the gas sensor 110 detects a predetermined gas (for example, when a detection signal of the gas sensor 110 indicates a predetermined value), the humidity controller 100 humidifies air in the humidity controller 100 so that, when the air in the humidity controller 100 is taken into the cooler 400 described below and cooled, the water vapor pressure of the cooled air becomes greater than or equal to the saturated water vapor pressure.

For example, when the gas sensor 110 detects a predetermined gas and the temperature and humidity sensor 120 detects that the temperature of air around the air purifying apparatus 1 is 25° C. and the relative humidity of the air is 50%, the humidity controller 100 humidifies the air in the humidity controller 100 so that the temperature of the air becomes 20° C. and the relative humidity of the air becomes 100%. Here, the temperature of the humidified air in the humidity controller 100 becomes lower than the temperature of air around the air purifying apparatus 1 because, when the humidifier 130 humidifies air, air in the humidity controller 100 is cooled due to vaporization of mist that is sprayed from the nozzle 131.

The cooler 400 includes a part of the shaft 10, a part of the outer wall 20, and the first blade fan 220A. Due to the airflow generated by the intake section 300, air whose humidity has been controlled flows into the cooler 400 from the humidity controller 100. In other words, as the shaft 10 rotates, the intake section 300 takes the air whose humidity has been controlled by the humidity controller 100 into the cooler 400. As the shaft 10 rotates, the first blade fan 220A rotates together with the shaft 10, and the cooler 400 causes a swirl of the air that has been taken in from the humidity controller 100 around the shaft 10. Then, centrifugal force acts on the air that swirls around the shaft 10, and a pressure difference is generated between air around the shaft 10 and air around the outer wall 20. Due to the pressure difference, the air around the shaft 10 adiabatically expands, and the air around the shaft 10 is cooled. That is, as the shaft 10 rotates, the cooler 400 causes a swirl of the air that has been taken in from the humidity controller 100 around the shaft 10 to generate a pressure difference between the air that has been taken in and that is adjacent to the shaft 10 and the air that has been taken in and that is adjacent to the outer wall 20, and thereby cools at least a part of the air that has been taken in.

For example, when air that has been controlled to have a temperature of 20° C. and a relative humidity of 100% is taken in from the humidity controller 100, the cooler 400 cools a part of the air that has been taken in and that is around the shaft 10 to 19° C.

The cooled air has a water vapor pressure that is greater than or equal to the saturated water. Therefore, in the cooled air, the water droplets 90 are generated with the dust particles 80 included in the cooled air as nuclei, and the generated water droplets 90 glow due to condensation on the dust particles 80 as nuclei. Then, a predetermined water-soluble gas dissolves in the grown water droplets 90. For example, due to condensation on nuclei, the water droplets 90 grow to each have a diameter of approximately several micrometers in a period of about 5 msec.

The separator 500 includes a part of the shaft 10, a part of the outer wall 20 including a portion having the discharge holes 21, and the second blade fan 220B. Due to the airflow generated by the intake section 300, air including the water droplets 90 in which a predetermined gas has dissolved flows into the separator 500 from the cooler 400. As the shaft 10 rotates, the second blade fan 220B rotates together with the shaft 10, and the separator 500 causes a swirl of the air, which has flowed from the cooler 400, around the shaft 10. Then, centrifugal force acts on air that swirls around the shaft 10, and the water droplets 90 are centrifugally separated from the air including the water droplets 90. The centrifugally separated water droplets 90 collide with the outer wall 20, move along the outer wall 20 due to the airflow generated by the intake section 300, and are discharged to the outside of the air purifying apparatus 1 from the discharge holes 21 of the outer wall 20. In this way, the separator 500 discharges a predetermined gas that is dissolved in the water droplets 90 and the dust particles 80 that have served as nuclei of condensation of the water droplets 90 to the outside of the air purifying apparatus 1 together with the water droplets 90.

Hereafter, an operation that the air purifying apparatus 1 performs when purifying air will be described with reference to a flowchart.

Figure 5:
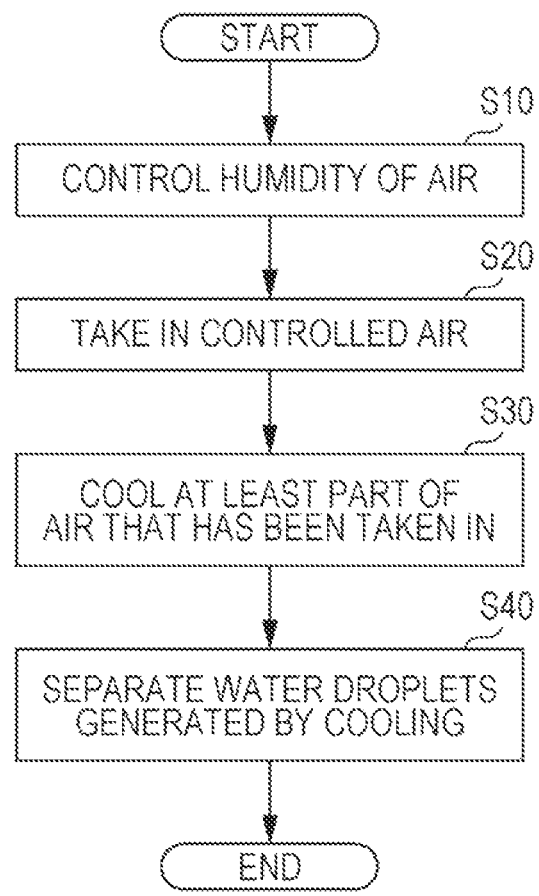
FIG. 5 is a flowchart of an operation performed by the air purifying apparatus according to the first embodiment.

FIG. 5 is a flowchart of the operation performed by the air purifying apparatus 1.

When the gas sensor 110 detects a predetermined water-soluble gas, the humidity controller 100 controls the humidity of air that has flowed from the outside of the air purifying apparatus 1, based on the temperature and humidity of air around the air purifying apparatus 1 detected by the temperature and humidity sensor 120 (step S10). At this time, the humidity controller 100 controls the humidity of the air so that, when the air in the humidity controller 100 is taken into the cooler 400 and cooled, the water vapor pressure of the cooled air becomes greater than or equal to the saturated water vapor pressure.

The intake section 300 generates airflow as the shaft 10 rotates, and takes the air whose humidity has been controlled by the humidity controller 100 into the cooler 400 (step S20).

The cooler 400 causes a swirl of the air that has been taken in around the shaft 10 as the shaft 10 rotates, and generates a pressure difference between the air that has been taken in and that is adjacent to the shaft 10 and the air that has been taken in and that is adjacent to the outer wall 20. By using the pressure difference, the cooler 400 causes at least a part of the air that has been taken in to adiabatically expand to cool the part of the air (step S30). Then, the water vapor pressure of the cooled air becomes greater than or equal to the saturated water vapor pressure, and the water droplets 90 are generated with the dust particles 80 as nuclei. At this time, a predetermined water-soluble gas dissolves in the water droplets 90. Then, air including the water droplets 90 into which the predetermined gas has dissolved flows into the separator 500 due to airflow generated by the intake section 300.

The separator 500 causes a swirl of the air including the water droplets 90, which has flowed from the cooler 400, around the shaft 10 as the shaft 10 rotates, and separates the water droplets 90 from the air including the water droplets 90 (step S40). A predetermined gas has been dissolved in the water droplets 90. The separated water droplets 90 are discharged to the outside of the air purifying apparatus 1 through the discharge holes 21.

As described above, the air purifying apparatus 1 can remove from air a water-soluble gas to be removed. Moreover, the air purifying apparatus 1 need not have a scrubber device, an activated carbon filter, a thermal storage layer, and the like, which are necessary for exiting air purifying apparatuses.

Accordingly, with the air purifying apparatus 1 configured as described above, it is possible to realize an air purifying apparatus having a configuration simpler than existing configurations.

Second Embodiment

Here, an air purifying apparatus 1A according to the second embodiment, which has a configuration that is partially changed from that of the air purifying apparatus 1 according to the first embodiment, will be described. Hereafter, components that are the same as those of the air purifying apparatus 1, which have been already described, will be denoted by the same numerals and detailed description of such components will be omitted; and mainly the difference from the air purifying apparatus 1 will be described.

Figure 6:
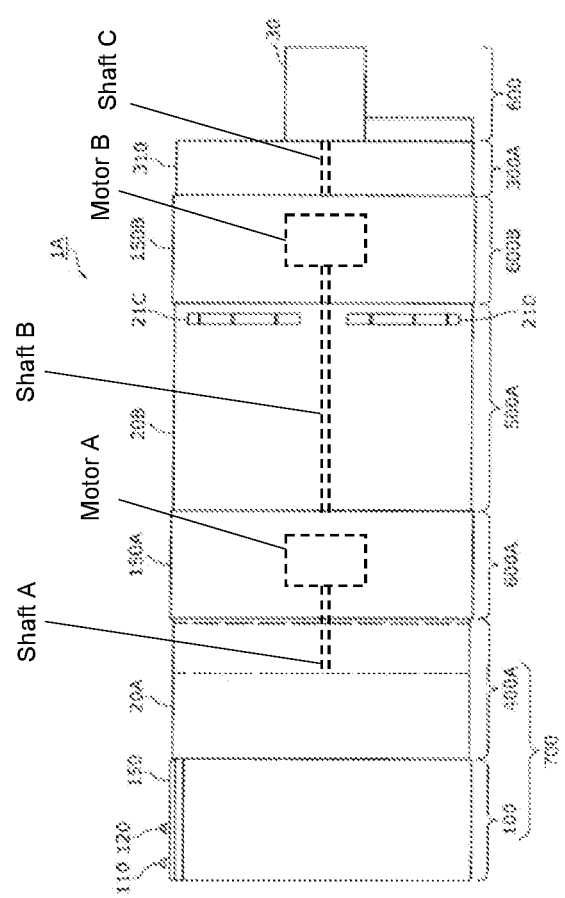
FIG. 6 is a side view of an air purifying apparatus according to a second embodiment.

FIG. 6 is a side view of the air purifying apparatus 1A.

As illustrated in FIG. 6, the air purifying apparatus 1A includes the humidity controller 100, a cooler 400A, a shaft rotator 600A, a separator 500A, a shaft rotator 600B, an intake section 300A, and the shaft rotator 600.

The cooler 400A differs from the cooler 400 according to the first embodiment in that the outer wall 20 is changed to an outer wall 20A and the shaft 10 is changed to a shaft A.

The outer wall 20A is an outer wall that is the same as the outer wall 20 except that the length of the outer wall 20A is less than the length of the outer wall 20 and that the outer wall 20A does not have the discharge holes 21. To be more specific, the outer wall 20A is an outer wall such that a portion of the outer wall 20 excluding a portion included in the cooler 400 according to the first embodiment is omitted from the outer wall 20.

The shaft A is a shaft that is the same as the shaft 10, except that the length of the shaft A is less than the length of the shaft 10 and that the shaft A is fixed to the shaft of a motor A, which is housed in the shaft rotator 600A described below, so that the shaft A can rotate together with the rotation shaft of the motor A. To be more specific, the shaft A is a shaft such that a portion of the shaft 10, excluding a portion included in the cooler 400 according to the first embodiment and a margin for fixing the shaft A to the rotation shaft of the motor A (hereafter, referred to as a "first margin"), is omitted from the shaft 10. When the gas sensor 110 detects a predetermined gas, the shaft rotator 600A may instruct the motor A to rotate the rotation shaft of the motor A.

The cooler 400A configured as described above performs an operation in the same way as the cooler 400 according to the first embodiment as the shaft A rotates.

The cooler 400A and the humidity controller 100 constitute a humidity control cooler 700.

Figure 7:
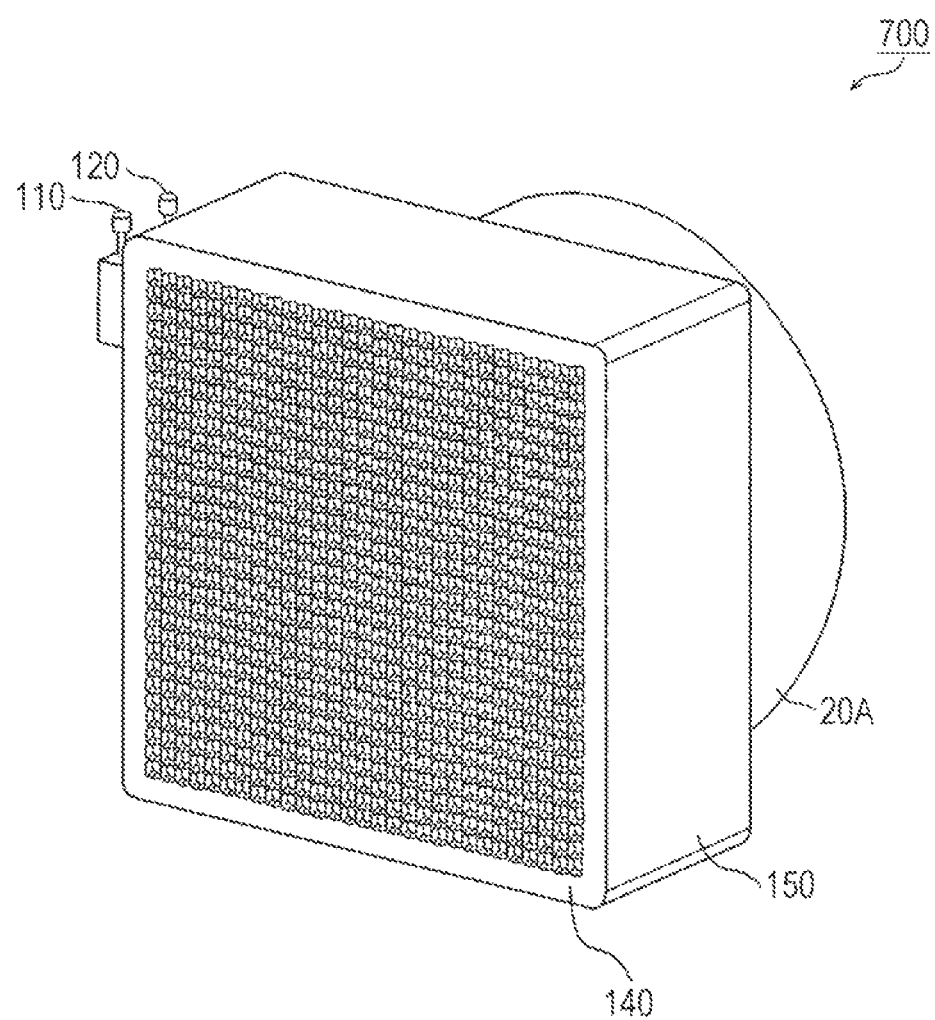
FIG. 7 is an external perspective view of a humidity control cooler according to the second embodiment.

FIG. 7 is an external perspective view of the humidity control cooler 700.

The shaft rotator 600A includes a tubular duct 150A whose cross section is a circle, the motor A, and the first margin of the shaft A.

The axis of the tubular duct 150A coincides with the axis of the outer wall 20A, and the circle of the cross section of the tubular duct 150A coincides with the circle of the cross section of the outer wall 20A.

The motor A is housed in the tubular duct 150A, and the shaft A is fixed to the rotation shaft of the motor A.

The shaft rotator 600A rotates the shaft A by instructing the motor A to rotate the rotation shaft of the motor A.

The separator 500A differs from the separator 500 according to the first embodiment in that the outer wall 20 is changed to an outer wall 20B and the shaft 10 is changed to a shaft B.

The outer wall 20B is an outer wall that is the same as the outer wall 20 except that the length of the outer wall 20B is less than the length of the outer wall 20. To be more specific, the outer wall 20B is an outer wall such that a portion of the outer wall 20 excluding a portion included in the separator according to the first embodiment is omitted from the outer wall 20.

The shaft B is a shaft that is the same as the shaft 10, except that the length of the shaft B is less than the length of the shaft 10 and that the shaft B is fixed to the shaft of a motor B, which is housed in the shaft rotator 600B described below, so that the shaft B can rotate together with the rotation shaft of the motor B. To be more specific, the shaft B is a shaft such that a portion of the shaft 10, excluding a portion included in the separator 500 according to the first embodiment and a margin for fixing the shaft B to the rotation shaft of the motor B (hereafter, referred to as a "second margin"), is omitted from the shaft 10. When the gas sensor 110 detects a predetermined gas, the shaft rotator 600B may instruct the motor B to rotate the rotation shaft of the motor B.

The separator 500A configured as described above performs an operation in the same way as the separator 500 according to the first embodiment as the shaft B rotates.

Figure 8:
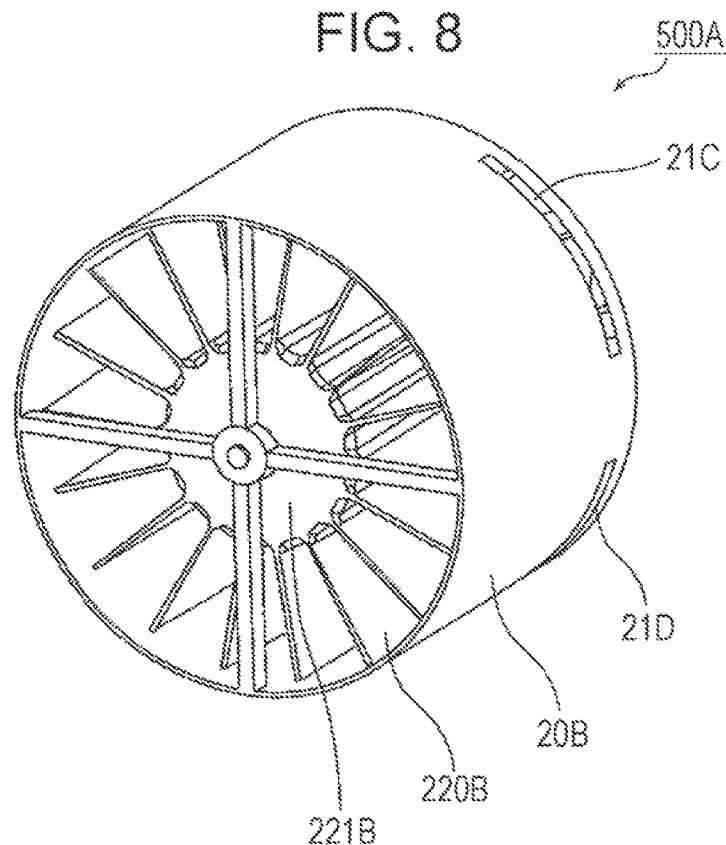
FIG. 8 is an external perspective view of a separator according to the second embodiment.

FIG. 8 is an external perspective view of the separator 500A.

The shaft rotator 600B includes a tubular duct 150B whose cross section is a circle, the motor B, and the second margin of the shaft B.

The axis of the tubular duct 150B coincides with the axis of the outer wall 20B, and the circle of the cross section of the tubular duct 150B coincides with the circle of the cross section of the outer wall 20B.

The motor B is housed in the tubular duct 150B, and the shaft B is fixed to the rotation shaft of the motor B.

The shaft rotator 600B rotates the shaft B by instructing the motor B to rotate the rotation shaft of the motor B.

The intake section 300A differs from the intake section 300 according to the first embodiment in that the shaft 10 is changed to a shaft C.

The shaft C is a shaft that is the same as the shaft 10 except that the length of the shaft C is less than the length of the shaft 10. To be more specific, the shaft C is a shaft such that a portion of the shaft 10, excluding a portion included in the intake section 300 according to the first embodiment and a margin for fixing the shaft C to the rotation shaft of the motor 31, is omitted from the shaft 10.

The intake section 300A configured as described above performs an operation in the same way as the intake section 300 according to the first embodiment as the shaft C rotates.

Figure 9:
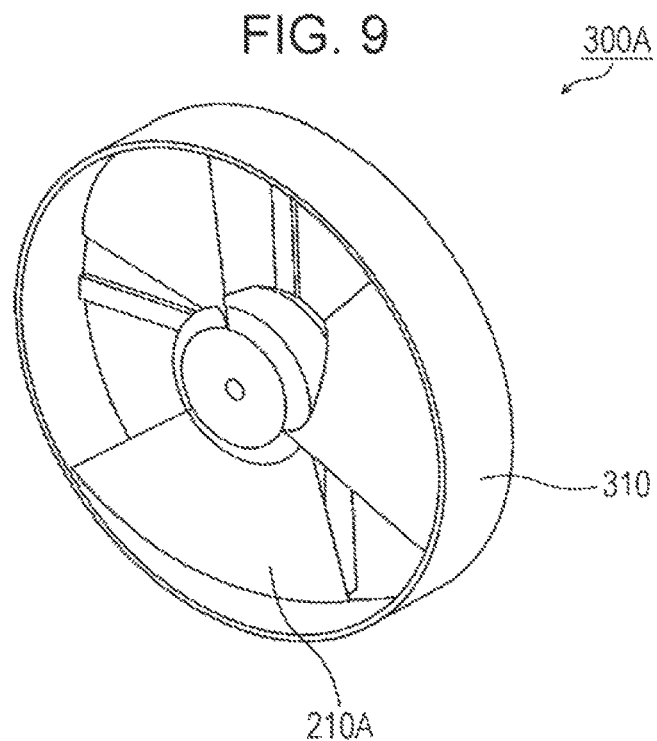
FIG. 9 is an external perspective view of an intake section according to the second embodiment.

FIG. 9 is an external perspective view of the intake section 300A.

As described above, the air purifying apparatus 1A includes the humidity controller 100, the cooler 400A that performs an operation in the same way as the cooler 400 according to the first embodiment, the separator 500A that performs an operation in the same way as the separator 500 according to the first embodiment, and the intake section 300A that performs an operation in the same way as the intake section 300 according to the first embodiment. Therefore, the air purifying apparatus 1A can perform an operation that is the same as the operation performed by the air purifying apparatus 1 according to the first embodiment.

In the air purifying apparatus 1A, the shaft A, the shaft B, and the shaft C are independent from each other; and the outer wall 20A and the outer wall 20B are independent from each other. Therefore, the air purifying apparatus 1A has high maintainability when maintenance that needs disassembly and assembly is performed.

Other Embodiments

Heretofore, the first embodiment and the second embodiment have been described as examples of the technology disclosed in the present disclosure. However, the technology according to the present disclosure is not limited to these examples, and is applicable to embodiments to which modifications, replacements, additions, and omissions are performed as necessary as long as such embodiments do not deviate from the spirit and scope of the present disclosure.

Hereafter, examples of modifications in the present disclosure will be enumerated.

(1) In the first embodiment, the intake cooling separator 200 is composed of three brocks, which are the intake section 300, the cooler 400, and the separator 500. However, the intake cooling separator 200 need not be composed of these three blocks. As an example, the intake cooling separator 200 may be composed of: a cooling separator that performs both of the operation performed by the cooler 400 and the operation performed by the separator 500; and the intake section 300. In this case, the cooling separator may include, instead of the first blade fan 220A and the second blade fan 220B, one blade fan for realizing both of the operation in step S30 and the operation in step S40.

As another example, the intake cooling separator 200 may be composed of: an intake cooler that performs both of the operation performed by the intake section 300 and the operation performed by the cooler 400; and the separator 500. In this case, the intake cooler may include, instead of the propeller fan 210 and the first blade fan 220A, one blade fan for realizing the operation in step S20 and the operation in step S30.

As another example, the intake cooling separator 200 may be composed of: an intake separator that performs both of the operation performed by the intake section 300 and the operation performed by the separator 500; and the cooler 400. In this case, the intake separator may include, instead of the propeller fan 210 and the second blade fan 220B, one blade fan for realizing the operation in step S20 and the operation in step S40.

As another example, the intake cooling separator 200 may perform, as one block, the operation performed by the intake section 300, the operation performed by the cooler 400, and the operation performed by the separator 500. In this case, the intake cooling separator 200 may include, instead of the propeller fan 210, the first blade fan 220A, and the second blade fan 220B, one blade fan for realizing three operations, which are the operation in step S20, the operation in step S30, and the operation in step S40.

(2) In the first embodiment, the cooler 400 includes the first blade fan 220A. However, the cooler 400 need not include the first blade fan 220A, as long as the cooler 400 can cause a swirl of the air that has been taken in from the humidity controller 100 around the shaft 10. For example, the cooler 400 that does not include the first blade fan 220A may be configured to cause a swirl of the air that has been taken in from the humidity controller 100 around the shaft 10 by using the viscosity of air around the shaft 10.

(3) In the first embodiment, the separator 500 includes the second blade fan 220B. However, the separator 500 need not include the second blade fan 220B, as long as the separator 500 can cause a swirl of the air that has been taken in from the cooler 400 around the shaft 10. For example, the separator 500 that does not include the second blade fan 220B may be configured to cause a swirl of the air that has been taken in from the cooler 400 around the shaft 10 by using the viscosity of air around the shaft 10.

(4) In the present disclosure, all or some of the functions and/or operations and/or control of each of the units, apparatuses, and devices may be executed by one or more electronic circuits including a semiconductor device, a semiconductor integrated circuit (IC), or a large-scale integration (LSI). An LSI or an IC may be integrated in one chip or may be configured as a combination of chips. For example, functional blocks other than storage elements may be integrated in one chip. Here, an integrated circuit such as an LSI or an IC may be called differently depending on the degree of integration, and may be referred to as a system LSI, a very large scale integration (VLSI), or an ultra large scale integration (ULSI). A field-programmable gate array (FPGA), which is an LSI that is programmed after being manufactured, or a reconfigurable logic device that allows reconfiguration of connection relationships inside an LSI or allows setting up of circuit segments inside an LSI may be also used for the same purpose.

(5) In the present disclosure, it is possible to execute all or some of the functions and/or operations and/or control of each of the units, apparatuses, and devices by software processing. In this case, software is recorded in one or more non-transitory recording media, such as ROMs, optical discs, or hard disk drives; and, when the software is executed by a processor, the software causes specific functions in the software to be executed by the processor and peripheral devices. The system or the device may include one or more non-transitory recording media on which the software is recorded, a processor, and required hardware devices such as an interface.

INDUSTRIAL APPLICABILITY

The present disclosure air is widely applicable to an apparatus that purifies air.

What is claimed is:

1. An air purifying apparatus comprising:
a humidifier for humidifying air;
a humidity controller that controls a humidity of the air; and
an intake cooling separator that includes one or more shafts and an outer wall that surrounds at least a part of the one or more shafts,
wherein the intake cooling separator generates airflow to obtain the humidity-controlled air, and thereby the intake cooling separator obtains the humidity-controlled air,
wherein the intake cooling separator includes a blade fan that swirls the humidity-controlled air around a first shaft included in the one or more shafts, and thereby the intake cooling separator generates a pressure difference between air included in the humidity-controlled air and around the first shaft, and air included in the humidity-controlled air and around the outer wall, and the pressure difference cools at least a part of the humidity-controlled air, and
wherein the one or more shafts are rotated along with the blade fan to cause the swirl, and to perform centrifugal separation of water droplets that are generated from the humidity-controlled air.

2. The air purifying apparatus according to claim 1,
wherein the humidity controller includes
a gas sensor that detects a predetermined gas, and
a temperature and humidity sensor that detects a temperature and a humidity of the air,
wherein the humidifier humidifies the air based on a result of detection by the gas sensor and a result of detection by the temperature and humidity sensor.

3. The air purifying apparatus according to claim 1,
wherein the outer wall has a discharge hole for discharging, to the outside, the water droplets.

4. The air purifying apparatus according to claim 1,
wherein the intake cooling separator includes a propeller fan,
wherein the propeller fan is attached to the first shaft and rotates when the first shaft rotates,
wherein the blade fan is attached to the first shaft and rotates when the first shaft rotates,
wherein rotation of the propeller fan generates the airflow, and
wherein rotation of the blade fan causes the swirl.

5. The air purifying apparatus according to claim 1,
wherein the one or more shafts include the first shaft, a second shaft, and a third shaft,
wherein the intake cooling separator includes
an intake section that includes the second shaft and generates the airflow,
a cooler that includes the first shaft and causes the swirl, and
a separator that includes the third shaft and performs the centrifugal separation, and
wherein the second shaft is rotated to generate the airflow, the first shaft is rotated to cause the swirl, and the third shaft is rotated to perform the centrifugal separation.

6. The air purifying apparatus according to claim 5,
wherein the intake section includes a propeller fan,
wherein the cooler includes the blade fan,
wherein the propeller fan is attached to the second shaft and rotates when the second shaft rotates,
wherein the blade fan is attached to the first shaft and rotates when the first shaft rotates,
wherein the rotation of the propeller fan generates the airflow, and
wherein the rotation of the blade fan causes the swirl.

7. An air purifying method comprising:
humidifying air;
controlling a humidity of the air;
generating airflow to transport humidity-controlled air, thereby obtaining the humidity-controlled air;
providing at least one blade fan for swirling the humidity-controlled air around a first shaft included in one or more shafts, thereby generating a pressure difference between air included in the humidity-controlled air and around the first shaft and air included in the humidity-controlled air and around an outer wall that surrounds at least a part of the one or more shafts, the pressure difference cooling at least a part of the humidity-controlled air; and
performing centrifugal separation of water droplets that are generated from the cooled humidity-controlled air,
wherein the one or more shafts are rotated to generate the airflow, to cause the swirl, and to perform the centrifugal separation, and
wherein the centrifugal separation is performed by the at least one blade fan.

* * * * *